(12) United States Patent
Leach (10) Patent No.: US 9,713,810 B2
(45) Date of Patent: Jul. 25, 2017

(54) CELL WASHING PLUNGER USING CENTRIFUGAL FORCE

(71) Applicant: Biomet Biologics, LLC, Warsaw, IN (US)

(72) Inventor: Michael D. Leach, Warsaw, IN (US)

(73) Assignee: Biomet Biologics, LLC, Warsaw, IN (US)

(*) Notice: Subject to any disclaimer, the term of this patent is extended or adjusted under 35 U.S.C. 154(b) by 199 days.

(21) Appl. No.: 14/672,335

(22) Filed: Mar. 30, 2015

(65) Prior Publication Data

US 2016/0288139 A1  Oct. 6, 2016

(51) Int. Cl.

| A61M 1/02 | (2006.01) |
|---|---|
| A61M 1/36 | (2006.01) |
| B01L 3/00 | (2006.01) |
| B04B 5/04 | (2006.01) |
| B04B 15/12 | (2006.01) |

(52) U.S. Cl.
CPC ............ *B01L 3/567* (2013.01); *A61M 1/0281* (2013.01); *A61M 1/3692* (2014.02); *A61M 1/3696* (2014.02); *B01L 3/502* (2013.01); *B04B 5/0442* (2013.01); *B04B 15/12* (2013.01)

(58) Field of Classification Search
CPC .............. A61M 1/0281; A61M 1/3692; A61M 1/3696; B01L 3/502; B01L 3/567; B04B 5/0442
See application file for complete search history.

(56) References Cited

U.S. PATENT DOCUMENTS

| 3,141,846 A | 7/1964 | Laven, Jr. |
|---|---|---|
| 3,409,165 A | 11/1968 | Creith |
| 3,420,374 A | 1/1969 | Umeda |
| 3,441,143 A | 4/1969 | Kudlaty |
| 3,453,364 A | 7/1969 | Flodin et al. |
| 3,469,369 A | 9/1969 | Helmke |
| 3,508,653 A | 4/1970 | Coleman |
| 3,593,915 A | 7/1971 | Steinacker |

(Continued)

FOREIGN PATENT DOCUMENTS

| AU | 696278 | 1/1999 |
|---|---|---|
| BR | 9103724 | 3/1993 |

(Continued)

OTHER PUBLICATIONS

"International Application Serial No. PCT/US2016/023762, International Search Report mailed Jun. 16, 2016", 4 pgs.

(Continued)

*Primary Examiner* — David A Reifsnyder
(74) *Attorney, Agent, or Firm* — Schwegman Lundberg & Woessner, P.A.

(57) ABSTRACT

Devices and methods for washing a suspension of cells are provided. The devices include concentric center, intermediate, and outer compartments. The center compartment and the intermediate compartment are in communication with each other by a first valve and the intermediate and outer compartments are in communication with each other by an opening, aperture, or second valve. The methods include loading a suspension of cells into the center compartment, loading a wash solution into the intermediate compartment, and rotating the device. Centripetal force forces cells through the wash solution and into the outer compartment, where they are isolated and collected.

29 Claims, 5 Drawing Sheets

(56) References Cited

U.S. PATENT DOCUMENTS

| | | |
|---|---|---|
| 3,647,070 A | 3/1972 | Adler |
| 3,779,383 A | 12/1973 | Ayres |
| 3,785,549 A | 1/1974 | Latham, Jr. |
| 3,814,248 A | 6/1974 | Lawhead |
| 3,850,369 A | 11/1974 | Bull et al. |
| 3,879,295 A | 4/1975 | Glover et al. |
| 3,894,952 A | 7/1975 | Ayres |
| 3,897,343 A | 7/1975 | Ayres |
| 3,909,419 A | 9/1975 | Ayres |
| 3,929,646 A | 12/1975 | Adler |
| 3,931,010 A | 1/1976 | Ayres et al. |
| 3,931,018 A | 1/1976 | North, Jr. |
| 3,935,113 A | 1/1976 | Ayres |
| 3,941,699 A | 3/1976 | Ayres |
| 3,972,812 A | 8/1976 | Gresl, Jr. |
| 3,982,691 A | 9/1976 | Schlutz |
| 4,001,122 A | 1/1977 | Griffin |
| 4,046,699 A | 9/1977 | Zine, Jr. |
| 4,055,501 A | 10/1977 | Cornell |
| 4,059,108 A | 11/1977 | Latham, Jr. |
| 4,077,396 A | 3/1978 | Wardlaw et al. |
| 4,152,270 A | 5/1979 | Cornell |
| 4,159,896 A | 7/1979 | Levine et al. |
| 4,187,979 A | 2/1980 | Cullis et al. |
| 4,204,537 A | 5/1980 | Latham, Jr. |
| 4,225,580 A | 9/1980 | Rothman et al. |
| 4,229,298 A | 10/1980 | Bange |
| 4,269,718 A | 5/1981 | Persidsky |
| 4,294,707 A | 10/1981 | Ikeda et al. |
| 4,298,598 A | 11/1981 | Schwarz et al. |
| 4,300,717 A | 11/1981 | Latham, Jr. |
| 4,303,193 A | 12/1981 | Latham, Jr. |
| 4,314,823 A | 2/1982 | Rich, Jr. et al. |
| 4,322,298 A | 3/1982 | Persidsky |
| 4,332,351 A | 6/1982 | Kellogg et al. |
| 4,362,567 A | 12/1982 | Schwarz et al. |
| 4,364,832 A | 12/1982 | Ballies et al. |
| 4,377,572 A | 3/1983 | Schwarz et al. |
| 4,414,976 A | 11/1983 | Schwarz et al. |
| 4,416,654 A | 11/1983 | Schoendorfer et al. |
| 4,417,981 A | 11/1983 | Nugent |
| 4,424,132 A | 1/1984 | Iriguchi |
| 4,427,650 A | 1/1984 | Stroetmann et al. |
| 4,427,651 A | 1/1984 | Stroetmann et al. |
| 4,442,655 A | 4/1984 | Stroetmann |
| 4,446,021 A | 5/1984 | Aufderhaar et al. |
| 4,453,939 A | 6/1984 | Zimmerman et al. |
| 4,464,167 A | 8/1984 | Schoendorfer et al. |
| 4,537,767 A | 8/1985 | Rothman et al. |
| RE32,089 E | 3/1986 | Blatt et al. |
| 4,610,656 A | 9/1986 | Mortensen |
| 4,617,009 A | 10/1986 | Ohlin et al. |
| 4,627,879 A | 12/1986 | Rose et al. |
| 4,631,055 A | 12/1986 | Redl et al. |
| 4,632,761 A | 12/1986 | Bowers et al. |
| 4,639,316 A | 1/1987 | Eldegheidy |
| 4,650,678 A | 3/1987 | Fuhge et al. |
| 4,655,211 A | 4/1987 | Sakamoto et al. |
| 4,672,969 A | 6/1987 | Dew |
| 4,675,117 A | 6/1987 | Neumann et al. |
| 4,680,025 A | 7/1987 | Kruger et al. |
| 4,714,457 A | 12/1987 | Alterbaum |
| 4,722,790 A | 2/1988 | Cawley et al. |
| 4,724,317 A | 2/1988 | Brown et al. |
| 4,735,616 A | 4/1988 | Eibl et al. |
| 4,735,726 A | 4/1988 | Duggins |
| 4,738,655 A | 4/1988 | Brimhall et al. |
| 4,755,300 A | 7/1988 | Fischel et al. |
| 4,755,301 A | 7/1988 | Bowers |
| 4,770,779 A | 9/1988 | Ichikawa et al. |
| 4,776,964 A | 10/1988 | Schoendorfer et al. |
| 4,818,291 A | 4/1989 | Iwatsuki et al. |
| 4,818,386 A | 4/1989 | Burns |
| 4,828,710 A | 5/1989 | Itoh et al. |
| 4,832,851 A | 5/1989 | Bowers et al. |
| 4,834,890 A | 5/1989 | Brown et al. |
| 4,839,058 A | 6/1989 | Cawley et al. |
| 4,844,818 A | 7/1989 | Smith |
| 4,846,780 A | 7/1989 | Galloway et al. |
| 4,846,974 A | 7/1989 | Kelley et al. |
| 4,853,137 A | 8/1989 | Ersson |
| 4,859,333 A | 8/1989 | Panzani |
| 4,871,462 A | 10/1989 | Fischel et al. |
| 4,874,368 A | 10/1989 | Miller et al. |
| 4,877,520 A | 10/1989 | Burns |
| 4,879,031 A | 11/1989 | Panzani et al. |
| 4,900,453 A | 2/1990 | Sedlmayer et al. |
| 4,902,281 A | 2/1990 | Avoy |
| 4,928,603 A | 5/1990 | Rose et al. |
| 4,929,242 A | 5/1990 | Desecki et al. |
| 4,933,291 A | 6/1990 | Daiss et al. |
| 4,943,273 A | 7/1990 | Pages et al. |
| 4,946,601 A | 8/1990 | Fiehler |
| 4,950,220 A | 8/1990 | Wells et al. |
| 4,957,638 A | 9/1990 | Smith |
| 4,983,157 A | 1/1991 | Pober et al. |
| 4,983,158 A | 1/1991 | Headley |
| 4,985,153 A | 1/1991 | Kuroda et al. |
| 5,000,970 A | 3/1991 | Shanbhag et al. |
| 5,002,571 A | 3/1991 | O'Donnell, Jr. et al. |
| 5,019,243 A | 5/1991 | McEwen et al. |
| 5,030,215 A | 7/1991 | Morse et al. |
| 5,030,341 A | 7/1991 | McEwen et al. |
| 5,045,048 A | 9/1991 | Kaleskas et al. |
| 5,053,127 A | 10/1991 | Schoendorfer et al. |
| 5,071,570 A | 12/1991 | Shiraki et al. |
| 5,100,564 A | 3/1992 | Pall et al. |
| 5,104,375 A | 4/1992 | Wolf et al. |
| 5,112,484 A | 5/1992 | Zuk, Jr. |
| 5,112,490 A | 5/1992 | Turpen |
| 5,131,907 A | 7/1992 | Williams et al. |
| 5,137,832 A | 8/1992 | Levine et al. |
| 5,141,645 A | 8/1992 | Shiraki et al. |
| 5,147,290 A | 9/1992 | Jonsson et al. |
| 5,152,905 A | 10/1992 | Pall et al. |
| 5,156,613 A | 10/1992 | Sawyer |
| 5,165,938 A | 11/1992 | Knighton |
| 5,171,456 A | 12/1992 | Hwang et al. |
| 5,173,295 A | 12/1992 | Wehling et al. |
| 5,185,001 A | 2/1993 | Galanakis |
| 5,188,583 A | 2/1993 | Guigan et al. |
| 5,190,057 A | 3/1993 | Sarfarazi |
| 5,190,759 A | 3/1993 | Lindblad et al. |
| 5,204,537 A | 4/1993 | Bennet et al. |
| 5,206,023 A | 4/1993 | Hunziker |
| 5,217,426 A | 6/1993 | Bacehowski et al. |
| 5,217,627 A | 6/1993 | Pall et al. |
| 5,219,328 A | 6/1993 | Morse et al. |
| 5,226,877 A | 7/1993 | Epstein |
| 5,234,608 A | 8/1993 | Duff |
| 5,236,604 A | 8/1993 | Fiehler |
| 5,258,126 A | 11/1993 | Pall et al. |
| 5,260,420 A | 11/1993 | Burnouf-Radosevich et al. |
| 5,269,927 A | 12/1993 | Fiehler |
| 5,271,852 A | 12/1993 | Luoma, II |
| 5,279,825 A | 1/1994 | Wehling et al. |
| 5,281,342 A | 1/1994 | Biesel et al. |
| 5,290,552 A | 3/1994 | Sierra et al. |
| 5,290,918 A | 3/1994 | Bui-Khac et al. |
| 5,298,171 A | 3/1994 | Biesel et al. |
| 5,304,372 A | 4/1994 | Michalski et al. |
| 5,316,674 A | 5/1994 | Pall et al. |
| 5,318,524 A | 6/1994 | Morse et al. |
| 5,318,782 A | 6/1994 | Weis-Fogh et al. |
| 5,321,126 A | 6/1994 | van Dommelen et al. |
| 5,322,620 A | 6/1994 | Brown et al. |
| 5,330,974 A | 7/1994 | Pines et al. |
| 5,344,752 A | 9/1994 | Murphy |
| 5,370,802 A | 12/1994 | Brown |
| 5,376,263 A | 12/1994 | Fischel |
| 5,387,187 A | 2/1995 | Fell et al. |
| 5,393,674 A | 2/1995 | Levine et al. |
| 5,395,923 A | 3/1995 | Bui-Khac et al. |
| 5,403,272 A | 4/1995 | Deniega et al. |

(56) References Cited

U.S. PATENT DOCUMENTS

| | | |
|---|---|---|
| 5,405,607 A | 4/1995 | Epstein |
| 5,411,885 A | 5/1995 | Marx |
| 5,417,650 A | 5/1995 | Gordon |
| 5,420,250 A | 5/1995 | Lontz |
| 5,443,481 A | 8/1995 | Lee |
| 5,454,958 A | 10/1995 | Fiehler |
| 5,456,693 A | 10/1995 | Conston et al. |
| 5,456,885 A | 10/1995 | Coleman et al. |
| 5,480,378 A | 1/1996 | Weis-Fogh et al. |
| 5,484,383 A | 1/1996 | Fitch, Jr. et al. |
| 5,494,578 A | 2/1996 | Brown et al. |
| 5,494,592 A | 2/1996 | Latham, Jr. et al. |
| 5,505,685 A | 4/1996 | Antwiler |
| 5,510,102 A | 4/1996 | Cochrum |
| 5,533,518 A | 7/1996 | Vogler |
| 5,560,830 A | 10/1996 | Coleman et al. |
| 5,577,513 A | 11/1996 | Van Vlasselaer |
| 5,585,007 A | 12/1996 | Antanavich et al. |
| 5,589,462 A | 12/1996 | Patat et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,905 A | 5/1997 | Haynes |
| 5,641,622 A | 6/1997 | Lake et al. |
| 5,643,192 A | 7/1997 | Hirsh et al. |
| 5,643,193 A | 7/1997 | Papillon et al. |
| 5,674,173 A | 10/1997 | Hlavinka et al. |
| 5,733,545 A | 3/1998 | Hood, III |
| 5,736,033 A | 4/1998 | Coleman et al. |
| 5,762,798 A | 6/1998 | Wenthold et al. |
| 5,788,662 A | 8/1998 | Antanavich et al. |
| 5,795,489 A | 8/1998 | Holm et al. |
| 5,795,571 A | 8/1998 | Cederholm-Williams et al. |
| 5,853,600 A | 12/1998 | McNeal et al. |
| 5,860,937 A | 1/1999 | Cohen |
| 5,889,584 A | 3/1999 | Wardlaw |
| 5,918,622 A | 7/1999 | Perez et al. |
| 5,924,972 A | 7/1999 | Turvaville et al. |
| 5,934,803 A | 8/1999 | Hutter |
| 5,958,253 A | 9/1999 | Holm et al. |
| 5,980,757 A | 11/1999 | Brown et al. |
| 6,011,490 A | 1/2000 | Tonnesen et al. |
| 6,022,306 A | 2/2000 | Dumont et al. |
| 6,025,201 A | 2/2000 | Zelmanovic et al. |
| 6,027,655 A | 2/2000 | Holm |
| 6,051,146 A | 4/2000 | Green et al. |
| 6,053,856 A | 4/2000 | Hlavinka |
| 6,054,122 A | 4/2000 | MacPhee et al. |
| 6,063,297 A | 5/2000 | Antanavich et al. |
| 6,071,423 A | 6/2000 | Brown et al. |
| 6,090,793 A | 7/2000 | Zimmermann et al. |
| 6,096,309 A | 8/2000 | Prior et al. |
| 6,102,843 A | 8/2000 | Kelley et al. |
| 6,117,425 A | 9/2000 | MacPhee et al. |
| 6,153,113 A | 11/2000 | Goodrich et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,274,090 B1 | 8/2001 | Coelho et al. |
| 6,277,961 B1 | 8/2001 | Hock et al. |
| 6,280,400 B1 | 8/2001 | Niermann |
| 6,296,602 B1 | 10/2001 | Headley |
| 6,316,247 B1 | 11/2001 | Katz et al. |
| 6,322,785 B1 | 11/2001 | Landesberg et al. |
| 6,334,842 B1 | 1/2002 | Hlavinka et al. |
| 6,342,157 B1 | 1/2002 | Hood, III |
| 6,368,298 B1 | 4/2002 | Beretta et al. |
| 6,464,624 B2 | 10/2002 | Pages |
| 6,472,162 B1 | 10/2002 | Coelho et al. |
| 6,516,953 B1 | 2/2003 | DiCesare et al. |
| 6,544,162 B1 | 4/2003 | Van Wie et al. |
| 6,563,953 B2 | 5/2003 | Lin et al. |
| 6,596,180 B2 | 7/2003 | Baugh et al. |
| 6,629,919 B2 | 10/2003 | Egozy et al. |
| 6,676,629 B2 | 1/2004 | Andrew et al. |
| 6,758,978 B1 | 7/2004 | Bedell |
| 6,764,531 B2 | 7/2004 | Hogan |
| 6,777,231 B1 | 8/2004 | Katz et al. |
| 6,830,762 B2 | 12/2004 | Baugh et al. |
| 6,905,612 B2 | 6/2005 | Dorian et al. |
| 6,979,307 B2 | 12/2005 | Beretta et al. |
| 7,011,644 B1 | 3/2006 | Andrew et al. |
| 7,077,273 B2 | 7/2006 | Ellsworth et al. |
| 7,179,391 B2 | 2/2007 | Leach et al. |
| 7,694,828 B2 | 4/2010 | Swift et al. |
| 7,708,152 B2 | 5/2010 | Dorian et al. |
| 7,824,559 B2 | 11/2010 | Dorian et al. |
| 7,901,584 B2 | 3/2011 | Dorian et al. |
| 7,987,995 B2 | 8/2011 | Dorian et al. |
| 8,096,422 B2 | 1/2012 | Dorian et al. |
| 8,105,495 B2 | 1/2012 | Dorian et al. |
| 8,133,389 B2 | 3/2012 | Dorian et al. |
| 2002/0032112 A1 | 3/2002 | Pages |
| 2002/0076400 A1 | 6/2002 | Katz et al. |
| 2003/0082152 A1 | 5/2003 | Hedrick et al. |
| 2003/0191429 A1 | 10/2003 | Andrew et al. |
| 2004/0171146 A1 | 9/2004 | Katz et al. |
| 2004/0182788 A1 | 9/2004 | Dorian et al. |
| 2004/0182795 A1 | 9/2004 | Dorian et al. |
| 2004/0251217 A1 | 12/2004 | Leach et al. |
| 2005/0076396 A1 | 4/2005 | Katz et al. |
| 2005/0084961 A1 | 4/2005 | Hedrick et al. |
| 2005/0109716 A1 | 5/2005 | Leach et al. |
| 2005/0153441 A1 | 7/2005 | Hedrick et al. |
| 2005/0153442 A1 | 7/2005 | Katz et al. |
| 2005/0196874 A1 | 9/2005 | Dorian et al. |
| 2005/0247715 A1 | 11/2005 | Ellsworth et al. |
| 2005/0260174 A1 | 11/2005 | Fraser et al. |
| 2005/0260175 A1 | 11/2005 | Hedrick et al. |
| 2005/0282275 A1 | 12/2005 | Katz et al. |
| 2006/0083720 A1 | 4/2006 | Fraser et al. |
| 2006/0175242 A1 | 8/2006 | Dorian et al. |
| 2006/0175244 A1 | 8/2006 | Dorian et al. |
| 2006/0196885 A1 | 9/2006 | Leach et al. |
| 2006/0243676 A1 | 11/2006 | Swift et al. |
| 2007/0036768 A1 | 2/2007 | Fraser et al. |
| 2007/0075016 A1 | 4/2007 | Leach |
| 2008/0011684 A1 | 1/2008 | Dorian et al. |
| 2008/0283474 A1 | 11/2008 | Leach et al. |
| 2009/0289014 A1 | 11/2009 | Hoeppner |
| 2010/0206798 A1 | 8/2010 | Dorian et al. |
| 2010/0226909 A1 | 9/2010 | Hecker et al. |
| 2014/0047986 A1 | 2/2014 | Robinson |
| 2016/0332158 A1 | 11/2016 | Leach et al. |

FOREIGN PATENT DOCUMENTS

| | | |
|---|---|---|
| CA | 1321138 | 8/1993 |
| CA | 2182862 | 6/1996 |
| CN | 1074709 | 7/1993 |
| DE | 56103 | 10/1860 |
| DE | 1443359 | 11/1968 |
| DE | 3321466 A1 | 12/1983 |
| DE | 4202667 | 5/1993 |
| EP | 090997 | 10/1983 |
| EP | 0097455 A2 | 1/1984 |
| EP | 0102773 | 3/1984 |
| EP | 0109374 | 5/1984 |
| EP | 0142339 | 5/1985 |
| EP | 0253198 | 1/1988 |
| EP | 0272915 A2 | 6/1988 |
| EP | 285891 | 10/1988 |
| EP | 0295771 | 12/1988 |
| EP | 0295771 A2 | 12/1988 |
| EP | 0417818 | 3/1991 |
| EP | 0534178 | 3/1993 |
| EP | 0592242 | 4/1994 |
| EP | 1005910 | 6/2000 |
| EP | 1427279 A1 | 6/2004 |
| EP | 1467746 A2 | 10/2004 |
| EP | 1670315 A2 | 6/2006 |
| EP | 1716901 | 11/2006 |

(56) References Cited

FOREIGN PATENT DOCUMENTS

| | | |
|---|---|---|
| GB | 854715 | 11/1960 |
| JP | 60-053845 | 3/1985 |
| JP | 60250014 A | 12/1985 |
| JP | 63182055 A | 7/1988 |
| JP | 6454256 | 4/1989 |
| JP | 2036872 | 2/1990 |
| JP | 02071747 | 3/1990 |
| JP | 04500170 T | 1/1992 |
| JP | 6250014 A | 9/1994 |
| JP | 09187504 A | 7/1997 |
| JP | 9509432 T | 9/1997 |
| JP | 11502502 T | 3/1999 |
| JP | 2000117150 A | 4/2000 |
| JP | 02129224 | 10/2000 |
| JP | 2001017540 A | 1/2001 |
| JP | 2005523128 T | 8/2005 |
| MX | 246078 | 5/2007 |
| WO | WO-8400905 | 3/1984 |
| WO | WO-8802259 | 4/1988 |
| WO | WO-8901827 A1 | 3/1989 |
| WO | WO-9010031 | 9/1990 |
| WO | WO-9222312 | 12/1992 |
| WO | WO-9305067 | 3/1993 |
| WO | WO-9308904 | 5/1993 |
| WO | WO-9407548 | 4/1994 |
| WO | WO-9616714 A1 | 6/1996 |
| WO | WO-9617871 A1 | 6/1996 |
| WO | WO-9848938 A1 | 11/1998 |
| WO | WO-0103756 | 1/2001 |
| WO | WO-0183068 | 11/2001 |
| WO | WO-0224107 | 3/2002 |
| WO | WO-03015800 | 2/2003 |
| WO | WO-03024215 A1 | 3/2003 |
| WO | WO-03/053362 A2 | 7/2003 |
| WO | WO-03/092894 | 11/2003 |
| WO | WO-03090839 A1 | 11/2003 |
| WO | WO-2004/009207 | 1/2004 |
| WO | WO-2004037427 A1 | 5/2004 |
| WO | WO-2004104553 | 12/2004 |
| WO | WO-2005034843 A2 | 4/2005 |
| WO | WO-2006081699 A1 | 8/2006 |
| WO | WO-2007142908 A1 | 12/2007 |
| WO | WO-2011008836 A1 | 1/2011 |
| WO | WO-2016160451 A1 | 10/2016 |
| WO | WO-2016182830 A1 | 11/2016 |

OTHER PUBLICATIONS

"International Application Serial No. PCT/US2016/023762, Written Opinion mailed Jun. 16, 2016", 5 pgs.
"U.S. Appl. No. 14/708,547, Non Final Office Action mailed Jan. 25, 2017", 8 pgs.
"U.S. Appl. No. 14/708,547, Non Final Office Action mailed Dec. 16, 2016", 9 pgs.
"U.S. Appl. No. 14/708,547, Response filed May 11, 2016 to Restriction Requirement mailed Mar. 11, 2016", 10 pgs.
"U.S. Appl. No. 14/708,547, Response filed Sep. 23, 2016 to Restriction Requirement mailed Jul. 28, 2016", 6 pgs.
"U.S. Appl. No. 14/708,547, Restriction Requirement mailed Mar. 11, 2016", 8 pgs.
"U.S. Appl. No. 14/708,547, Restriction Requirement mailed Jul. 28, 2016", 6 pgs.
"International Application Serial No. PCT/US2016/030880, International Search Report mailed Oct. 5, 2016", 7 pgs.
"International Application Serial No. PCT/US2016/030880, Invitation to Pay Additional Fees and Partial Search Report mailed Aug. 12, 2016", 6 pgs.
"International Application Serial No. PCT/US2016/030880, Written Opinion mailed Oct. 5, 2016", 9 pgs.

CELL WASHING PLUNGER USING CENTRIFUGAL FORCE

FIELD

The present disclosure relates to washing a suspension of cells, and particularly to washing cells with centrifugal force.

BACKGROUND

This section provides background information related to the present disclosure which is not necessarily prior art.

Blood transfusions are used to treat many disorders and injuries, such as in the treatment of accident victims and during surgical procedures. According to current American Red Cross statistics, about 5 million people receive blood transfusions each year, in the United States alone. Thus, health care systems rely on the collection and distribution of blood. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during a medical procedure.

Donated blood is typically processed into components and then placed in storage until needed. When a subject is in need of a blood transfusion, a unit of blood is commonly removed from storage, rejuvenated, washed, and resuspended in an appropriate solution. In some instances, the red blood cells were lyophilized prior to storage, in which case they need to be resuspended, washed, and then resuspended again in an appropriate solution. The resuspended red blood cells are then transfused into the subject. In either scenario, washing the red blood cells is traditionally a tedious, time consuming and multistep process that requires a great deal of tubing, and the use of expensive centrifuges with rotating seals to separate the cells from the wash solution. Therefore, there remains a need to streamline and simplify the process for washing red blood cells prior to transfusion.

SUMMARY

This section provides a general summary of the disclosure, and is not a comprehensive disclosure of its full scope or all of its features.

The present technology provides a device for washing a suspension of cells. The device includes a cylindrical inner wall that extends about and along a longitudinal axis from a first end to a second end that defines a central compartment. The device also includes a cylindrical intermediate wall that extends about and along the axis from the first end to the second end that defines an intermediate compartment. Also, the device has a cylindrical outer wall that extends about and along the axis from the first end to a third end that defines an outer wall. The central, intermediate, and outer compartments are concentric. Additionally, a first valve is positioned through the first inner wall near the second end such that the central compartment is in fluid communication with the intermediate compartment when the valve is open. An aperture or second valve is positioned through the second inner wall near the first end such that the intermediate compartment is in fluid communication with the outer compartment continuously or when the second valve is open. First and second inlets are positioned on the first end and are in communication with the center and intermediate compartments, respectively. An outlet is positioned on the first end and is in communication with the outer compartment.

Another device for washing a suspension of cells is also provided. The device has an annular intermediate wall extending about and along a longitudinal axis from a first surface to a second opposing surface; an annular inner wall extending about and along the axis from the first surface to the second surface; and an annular outer wall extending about and along the axis from the first surface to a third surface that extends outwardly and orthogonally from the intermediate wall. The annular inner wall defines a first central compartment, and the annular intermediate and outer walls define a second intermediate compartment and a third outer compartment. The first, second and third compartments are concentric. First and second inlets are positioned on the first end and are in communication with the center and intermediate compartments, respectively. An outlet is positioned on the first end and is in communication with the outer compartment.

Also, the present technology provides a method for washing a suspension of cells. The method includes introducing a suspension of cells into a central cylindrical compartment of a device for washing cells. The suspension of cells includes a suspension fluid and a plurality of cells. The method further includes introducing a wash solution into an annular intermediate compartment of the device, wherein the intermediate compartment is adjacent to the central compartment, and wherein the central compartment is separated from the intermediate compartment by a valve. Then, the method includes rotating the device about a central longitudinal axis such that the wash solution is forced outward through an aperture and into an annular outer compartment, wherein the outer compartment is adjacent to the intermediate compartment. The method then includes opening the valve, separating the cells from the suspension fluid, isolating the cells, and collecting the cells.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present technology generally provides devices and methods for washing a suspension of cells. The devices and methods rely on centripetal force to pass "dirty" cells through a wash solution. The cells are then isolated from the wash solution as "clean cells". Accordingly, the devices according to the present technology do not require much, if any, tubing. Rotating seals are not required in the device and the only movements necessary are spinning of a rotor and opening of at least one valve as described in detail below. The devices provide quick and easy methods for washing a suspension of cells, which, for example, can be administered to a human or other animal subject in need thereof.

The devices can be used to separate a component from a multicomponent mixture. For example, cells can be separated from a multicomponent mixture in order to separate the cells from at least one unwanted component, which results in washed cells. Different types of cells are often treated with various compositions, which results in a need to separate the cells from treatment solutions and particulate matter, such as cell fragments and cellular debris. According to the present technology, cells can be washed in any wash solution known in the art. However, in various embodiments the wash solution is not less dense than the fluid in which the cells are suspended. In other embodiments, the wash solution is denser than the fluid in which the cells are suspended. Non-limiting examples of wash solutions include water, saline, dextrose, saline with 5% dextrose, phosphate buffered saline, and other solution that are used to remove unwanted components from cells. The cells may then be administered to a subject, such as a human or non-human mammal, or otherwise manipulated or stored. Non-limiting examples of cells that can be treated and washed include cells in whole blood, red blood cells, platelets, adipocytes, chondrocytes, and mixtures thereof. For example, because stored red blood cells (RBCs) have a diminished capacity to oxygenate tissues, a suspension of RBCs removed from storage can be rejuvenated by adding an enhancement composition, such as Rejuvesol® Red Blood Cell Processing Solution (Citra Labs, LLC, Braintree, Mass.), to the RBCs to form a multicomponent mixture or a suspension of cells. The suspension of cells including rejuvenated RBCs and a wash solution are then introduced into a device provided herein, wherein the RBCs are washed. During the wash, the RBCs are separated and isolated from the enhancement composition and optionally from unwanted cellular debris. The RBCs can then be used as concentrated RBCs or they can be resuspended in a reconstitution solution to achieve a desired RBC concentration.

Methods

Figure 1:
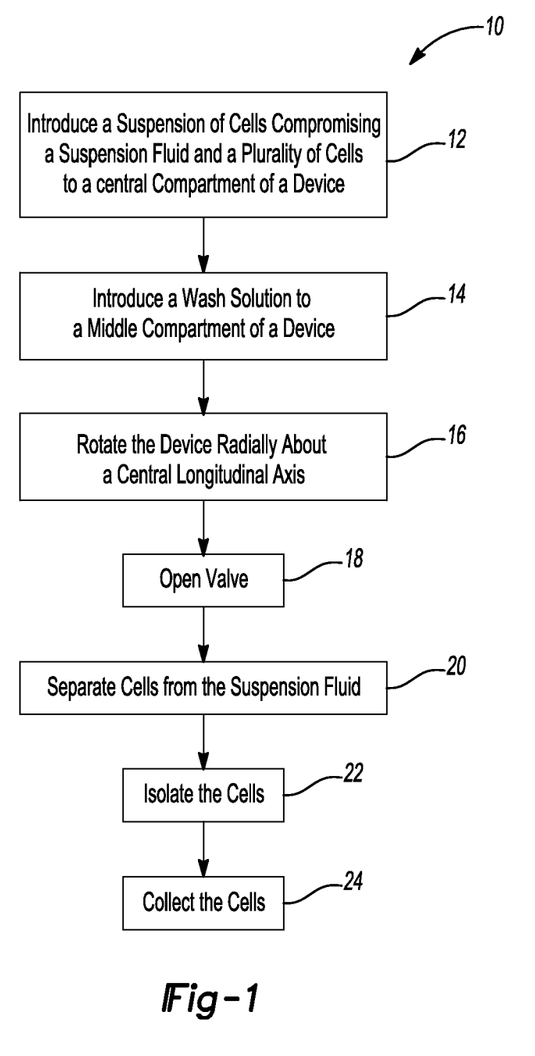
FIG. 1 is a flow chart showing a method for washing a suspension of cells.

With reference to FIG. 1, the present technology provides a method 10 for washing a suspension of cells. The suspension of cells includes a suspension fluid and a plurality of cells. As shown at block 12, the method 10 comprises introducing a suspension of cells into a central cylindrical compartment of a cell-washing device. In various embodiments, introducing a suspension of cells into the central compartment comprises introducing a suspension of cells comprising a suspension fluid and a plurality of cells selected from the group consisting of red blood cells, white blood cells, platelets, adipocytes, chondrocytes, and mixtures thereof into the central compartment. In some embodiments, the suspension of cells comprises a plurality of red blood cells and an enhancement composition, such as, for example, Rejuvesol® Red Blood Cell Processing Solution (Citra Labs, LLC, Braintree, Mass.). However, it is understood that the cell types described herein are non-limiting and that any type of cell can be washed according to the current technology.

As shown in block 14, the method 10 also includes introducing a wash solution into an annular intermediate compartment of the device, wherein the intermediate compartment is adjacent to the central compartment. The central compartment is separated from the intermediate compartment by a first valve. In various embodiments, introducing a wash solution to the intermediate compartment comprises introducing a wash solution selected from the group consisting of water, saline, dextrose, saline with 5% dextrose, and phosphate buffered saline into the intermediate compartment. In some embodiments, the wash solution has a density equal to or greater than the density of a fluid in which the cells to be washed are suspended. This density requirement enables the cells in the suspension to move from the suspension fluid to the wash solution with minimal mixing of the suspension fluid with the wash solution.

The method 10 also comprises rotating the device radially about a central longitudinal axis at a first speed to generate a first centripetal force, as shown in block 16. In some embodiments, the first centripetal force that causes the wash to move outward and into an annular outer compartment that is adjacent to the intermediate compartment by way of an aperture, opening, or optional second valve. When the second valve is present, it is actuated mechanically or by a predetermined centripetal force, such as the first centripetal force. In yet other embodiments, introducing the wash solution to the device includes introducing a sufficient volume of wash solution to fill the intermediate and outer compartments, which are in fluid communication through an aperture or opening. In such embodiments, the first centripetal force has a minimal effect on how the wash solution is distributed between the intermediate and outer compartments.

As shown in blocks 18 and 20, the method 10 also comprises opening the valve and separating the plurality of cells from the suspension fluid. Opening the valve occurs when the device is rotated to a second speed that generates a second centripetal force. In various embodiments, the valve is positioned such that the cells move out of the suspension fluid in the central compartment and enter the intermediate compartment at a lower end. Because the wash solution has a density equal to or greater than the density of the suspension fluid, a minimal amount of suspension fluid should enter the intermediate compartment. The cells are forced through the wash solution in the intermediate compartment and upward toward the aperture, opening, or optional second valve. By being separated from the suspension fluid and traveling through the wash solution, the cells are washed and become "clean".

As shown in block 22, the method 10 then comprises isolating the washed cells. Isolating the washed cells occurs when the cells travel through the aperture, opening, or optional second valve and into the outer compartment. The cells have a density that is greater than the density of the wash solution. Therefore, as the cells enter the outer compartment, they displace the wash solution, which is forced through the aperture, opening, or optional second valve in an opposite direction of the cells to enter the intermediate compartment. This displacement may also cause a portion of the wash solution in the intermediate compartment to enter the central compartment through the valve separating the compartments. Isolating is complete when all the cells have entered the outer compartment and the outer compartment contains a minimal volume or no wash solution. Then, rotation of the device is stopped, and as shown in block 24, the method 10 includes collecting the cells through an outlet that is in fluid communication with the outer compartment.

Devices

Figure 2:
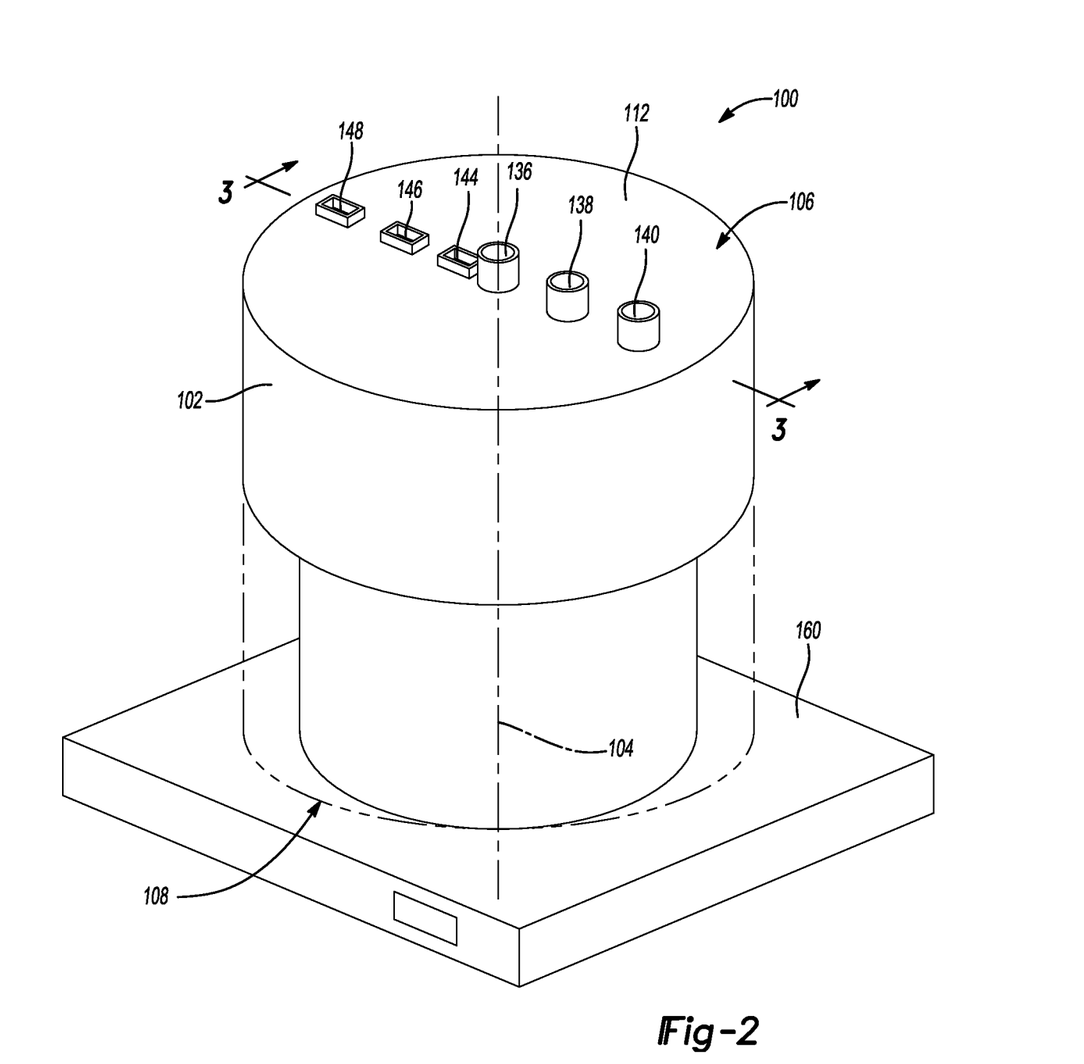
FIG. 2 is a perspective view of a device for washing a suspension of cells.
Figure 3:
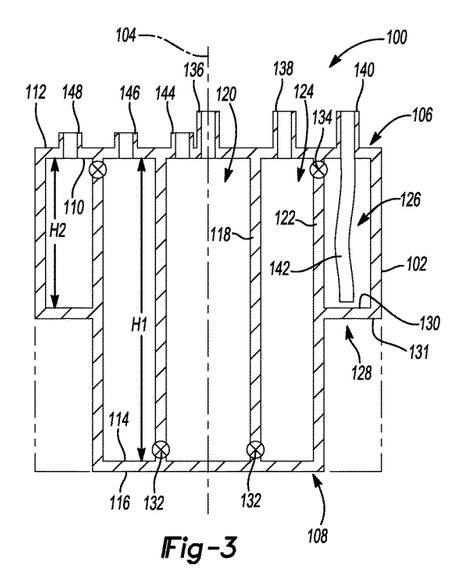
FIG. 3 is a cross-sectional view of the device shown in FIG. 2 taken along line 3.

With reference to FIG. 2, the present technology provides a device 100 that can be used to perform the method 10 for washing a suspension of cells of FIG. 1. FIG. 3 is a cross-sectional view of the device 100 shown in FIG. 2 taken along line 3. The device 100 comprises a cylindrical or annular outer 102 wall that extends about and along a longitudinal central axis 104 from a first end 106 to a second end 108 or to a third end 128. The first end 106 includes a first inner surface 110 and a first outer surface 112 and the second end 108 includes a second inner surface 114 and a second outer surface 116. The third end includes a third inner surface 130 and a third outer surface 131. In various embodiments, the first, second, and third ends 106, 108, 128 are planar. Additionally, as discussed further below, the second and third ends 108, 128 can be equidistant from the first end 106, or the distance between the second end 108 and the first end 106 can be longer than the distance between the third end 128 and the first end 106.

The device 100 also comprises a first cylindrical inner wall 118 that extends about and along the axis 104 from the first end 106 to the second end 108. The first inner wall 118 contacts the first end 106 at the first inner surface 110 and the second end 108 at the second inner surface 114. The first inner wall 118 defines a first central compartment 120. Also, the device 100 comprises a second intermediate cylindrical inner wall 122 that extends about and along the axis 104 from the first end 106 to the second end 108. The second intermediate inner wall 122 contacts the first end 106 at the first inner surface 110 and the second end 108 at the second inner surface 114 and is positioned between the inner wall 118 and the outer wall 102 and defines an intermediate annular compartment 124 and an outer annular compartment 126. The central compartment 120, the intermediate compartment 124, and the outer compartment 126 are concentric.

In various embodiments, the first end 106 and the second end 108 are separated by a distance H1 with respect to the central, intermediate and outer compartments 120, 124, 126. In other words, the inner wall 118, intermediate wall 122, and outer wall 102 each extend a distance H1 from the first end 106 to the second end 108. In other embodiments, the first end 106 and second end 108 are separated by a distance H1 with respect to the central and intermediate compartments 120, 124 and by a distance of H2 with respect to the outer compartment 126, wherein H1 is greater than H2. In other words, the inner and intermediate walls 118, 122 both extend a distance H1 from the first end 106 to the second end 108 and the outer wall extends a distance H2 from the first end 106 to the third end 128. In such embodiments, the third end 128 extends outwardly and optionally orthogonally from the intermediate wall 122 to the outer wall 102 to define the outer compartment 126. In various embodiments, H2 is from about 95% the height of H1 to about 5% the height of H1. For example, H2 can be about 95% (about ¹⁹⁄₂₀), about 90% (about ⁹⁄₁₀), about 80% (about ⅘), about 75% (about ¾), about 66% (about ⅔), about 50% (about ½), about 40% (about ⅖), about 33% (about ⅓), about 25% (about ¼), about 20% (about ⅕), about 10% (about ¹⁄₁₀), or about 5% (about ¹⁄₂₀) the height of H1. When the second end 108 and the third end 128 are equidistant from the first end 106, i.e., both at a distance H1 from the first end 106, the second end 108 and third end 128 are equivalent and there may be little or no distinction between the second and third ends 108, 128. In any embodiment, the volume of the inner compartment 120 is equal to or greater than the volume of the outer compartment 126, such that the outer compartment can receive all or a majority of cells loaded in the first compartment 120, as described further below.

The device 100 also includes a first valve 132 positioned in or through the inner wall 118 at or near the second inner surface 114 of the second end 108. In various embodiments, the device 100 comprises a plurality of first valves 132. The central and intermediate compartments are in fluid communication with each other when the first valve 132 is open. The first valve 132 is configured to open mechanically or centripetally at a predetermined centripetal force. In various embodiments, the first valve 132 opens when the device 100 is spun at a speed of from about 500 to about 3000 rpm, or from about 1000 to about 2000 rpm. In one embodiment, the first valve opens when the device is spun at a speed of at least about 500 rpm. Non-limiting examples of valves that are actuated by centripetal force and that are suitable for the first valve 132 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference.

The device 100 also includes an aperture, opening, or second valve 134 positioned in or through the intermediate wall 122 at or near the first inner surface 110 of the first end 106 to establish an optionally controllable fluid communication between the intermediate and outer compartments 124, 126. In various embodiments, the device 100 comprises a plurality of apertures, openings, or second valves 134. In other embodiments, the aperture, opening, or second valve 134 is an annular and continuous opening that provides continuous and uninterrupted fluid communication between the intermediate and outer compartments. In yet other embodiments, the aperture, opening, or second valve 134 comprises a second valve that establishes fluid communication between the intermediate and outer compartments 124, 126, which is controlled by actuating the valve to an open position. In such embodiments, the second valve 134 is configured to open mechanically or at a predetermined centripetal force. In various embodiments, the second valve 134 opens when the device 100 is spun at a speed of from about 500 to about 3000 rpm, or from about 1000 to about 2000 rpm. In one embodiment, the first valve opens when the device is spun at a speed of at least about 500 rpm. Non-limiting examples of valves that are actuated by centripetal force and that are suitable for the second valve 134 are described in U.S. Pat. No. 7,824,559 issued to Dorian et al. on Aug. 10, 20016, and U.S. Pat. No. 7,708,152 issued to Dorian et al. on May 4, 2010, both of which are incorporated herein by reference.

Figure 4:
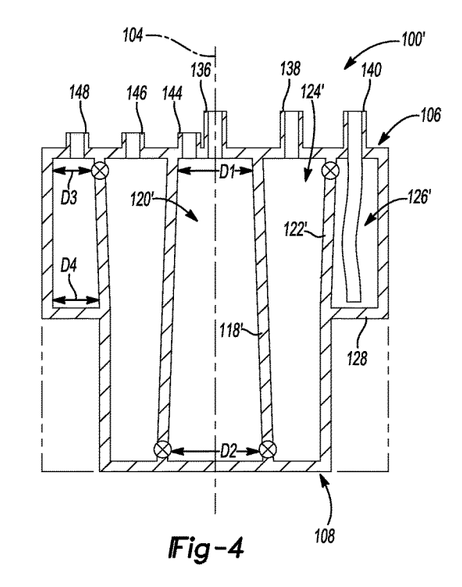
FIG. 4 is a is a cross-sectional view of a device that is similar to the device shown in FIG. 3, but having slanted or sloped walls.

As shown in FIG. 3, the inner wall 118 and intermediate wall 122 are parallel to the axis 104. However, in some embodiments, the inner wall 118 and intermediate wall 122 are slanted or sloped so as to encourage migration of cells in a predetermined direction. In this regard, FIG. 4 shows a device 100' that is similar to the device 100'. However, the device 100' has a slanted or sloped inner wall 118' that is not parallel to the axis 104, which defines a central compartment 120'. Here, the central compartment 120' has a diameter D1 at or near the first end 106 and a diameter D2 at or near the second end 108, wherein D2 is greater than D1. The difference between D2 and D1 results in a slant or angle of from about 0.1° to about 5° with respect to the axis 104. When the first compartment 120' is filled with a suspension of cells and the device 100' is rotating radially about and perpendicular to the axis 104, the slant or slope encourages the cells to migrate downward and outward toward the first valve 132. Additionally, the device 100' can have a slanted or sloped intermediate wall 122' that is not parallel to the axis 104, which defines an intermediate compartment 124' and an outer compartment 126'. Here the outer compartment 126' has a diameter D3 at or near the first end 106 and a diameter D2 at or near the second end 108 or the portion of the second end 128, wherein D4 is greater than D3. The difference between D4 and D3 results in a slant or angle of from about 0.1° to about 5° with respect to the axis 104. When the device 100' is rotating, the slant or angle of the intermediate wall 122' encourages cells to migrate upward and outward toward the aperture, opening, or second valve 134.

Referring back to FIGS. 2 and 3, the device 100 comprises a first inlet 136 and a second inlet 138. The first inlet 136 is positioned at the first end 106 and is in communication with the central compartment 120. The second inlet 138 is also positioned at the first end 106, but is in communication with the intermediate compartment 124. Therefore, the first inlet 136 is configured to permit introducing a suspension of cells into the central compartment 120 and the second inlet 138 is configured to permit introducing a wash solution into the intermediate compartment 124. The device further comprises an outlet 140 positioned at the first end 106 and in communication with the outer compartment 126. In some embodiments, the outlet 140 is in communication with the outer compartment 126 by way of a conduit 142 that extends downward from the outlet 140 to or near the second or third inner surface 114, 130. The conduit 142 is configured such that from about 75% to about 100% of the contents of the third compartment 126 can be removed through the outlet 140.

Additionally, the device 100 comprises a first vent 144, a second vent 146, and a third vent 148 that are in communication with the central compartment 120, intermediate compartment 124, and outer compartment 126, respectively. The vents 144, 146, 148 permit air to escape the respective compartments 120, 124, 126 as they become filled with wash solution, a suspension of cells, cell, or a mixture thereof. In some embodiments (not shown) the vents are integrated into the inlets and outlet such that separate inlets, outlets, and vents are not required. Moreover, the inlets, outlet, vents, or combinations thereof (inlet/vent or outlet/vent) can be positioned at the first end 106 such that the device is balanced when rotating radially about the axis 104.

The devices 100, 100' are configured to be received by a base unit 160 that comprises a rotor. When engaged with the base unit 160, the base unit 160 is capable of spinning the devices 100, 100' about the axis 16 at various speeds to generate various centripetal forces.

Methods for Using the Devices

Figure 5:
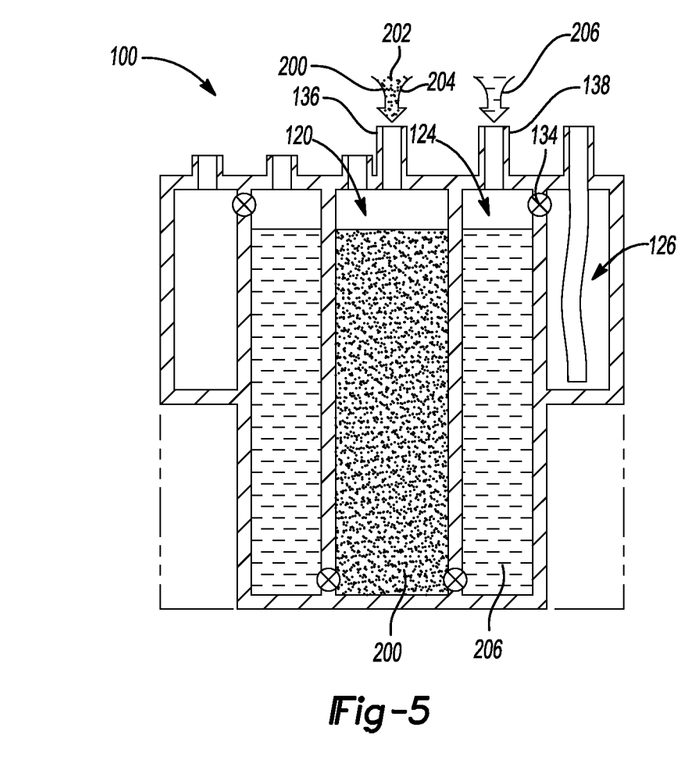
FIGS. 5-8 are graphic illustrations of various stages of the device of FIGS. 2-4 being used to wash a suspension of cells.

With reference to FIGS. 5-8, the current technology provides methods for using the devices 100, 100' of FIGS. 2-4 to perform a method for washing a suspension of cells that is consistent with the method 10 described in regard to FIG. 1. Although FIGS. 5-8 show the device 100 of FIGS. 2 and 3 in use, the method can be performed with the device 100' of FIG. 4 without any or substantial modification. As shown in FIG. 5, the method comprises introducing or loading a suspension of cells 200 that includes a suspension fluid 202 and a plurality of cells 204 into the central compartment 120 of the device 100 via the first inlet 136. As described above, the cells can be a plurality of any cell that requires washing. Non-limiting examples of cells include red blood cells, white blood cells, platelets, chondrocytes, adipocytes, and mixtures thereof. The suspension fluid can be any fluid known in the art, and can include an enhancement composition, such as Rejuvesol® Red Blood Cell Processing Solution (Citra Labs, LLC, Braintree, Mass.). In one embodiment, an enhancement composition is preloaded into the central compartment 120 of the device 100 and then red blood cells are introduced to the central compartment 120. The red blood cells are incubated with the enhancement composition to generate a suspension of cells, wherein the enhancement composition is a component of the suspension fluid.

The method also includes introducing or loading a wash solution 206 into the intermediate compartment 124 of the device 100 via the second inlet 138 until at least the intermediate compartment 124 is full of wash solution 206. In one embodiment, the intermediate and outer compartments 124, 126 are in continuous fluid communication with each other via the aperture, opening, or second valve 134 such that loading is performed until both the intermediate and outer compartments 124, 126 are filled with the wash solution 206. As described above, non-limiting examples of suitable wash solutions include water, saline, dextrose, saline with 5% dextrose, phosphate buffered saline. Nonetheless, in one embodiment, the wash solution 206 can be any solution that has a density equal to or greater than the density of the suspension fluid 202. Loading the suspension of cells 200 and wash solution 206 can be performed by any method known in the art, such as, for example, by injecting with a syringe or by pumping the suspension 200 and wash solution 206 individually through a conduit that is coupled to the inlets 136, 138.

Figure 6:
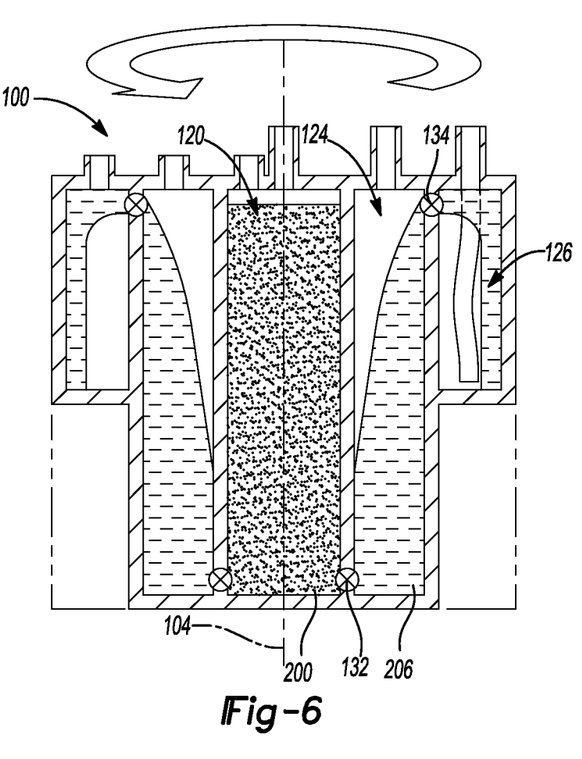

With reference to FIG. 6, the method comprises coupling the device 100 to a base unit, such as the base unit 160 shown in FIG. 2, and rotating the device 100 radially about the central axis 104 in either a clockwise or counter-clockwise direction. In one embodiment where the device 100 includes a second valve 134, the device 100 is rotated to a first speed to generate a first centripetal force. The first centripetal force triggers the second valve to open, wherein wash solution 206 is forced from the intermediate compartment 124 to the outer compartment 126. In various embodiments, the second valve 134 opens when the device 100 is spun at a speed of from about 500 to about 3000 rpm, or from about 1000 to about 2000 rpm. In one embodiment, the first valve opens when the device is spun at a speed of at least about 500 rpm. In embodiments where the intermediate and outer compartments 124, 126 are in continuous fluid communication with each other via the aperture or opening 134, and wherein both the intermediate and outer compartments 124, 126 are filled with the wash solution 206, rotating at the first speed has a minimal effect on the distribution of the wash solution 206 throughout the intermediate and outer compartments 124, 126.

Figure 7:
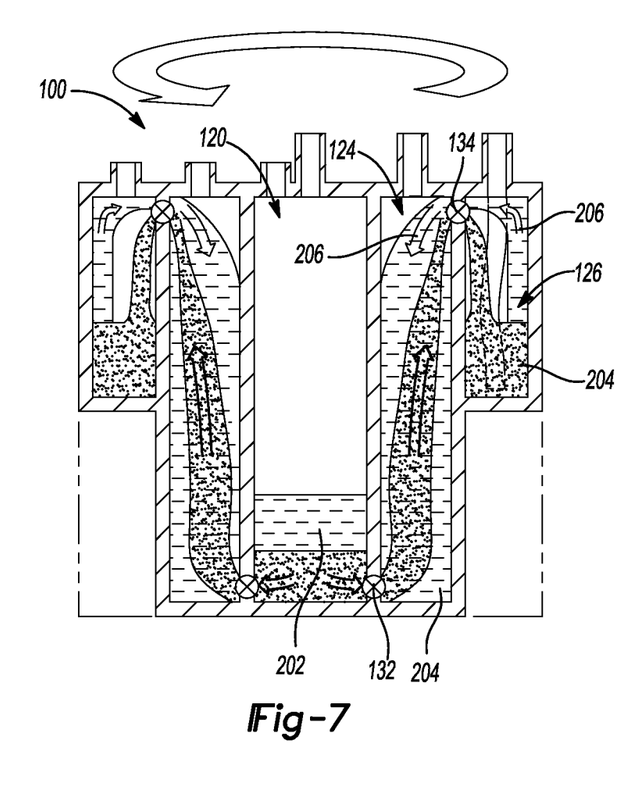

As shown in FIG. 7, the method comprises opening the first valve 132 and separating the cells 204 from the suspension fluid 202. In various embodiments, opening the first valve 132 comprises rotating the device 100 to a second speed to generate a second centripetal force, wherein the second centripetal force triggers the first valve 132 to open. In various embodiments, the first valve 132 opens when the device 100 is spun at a speed of from about 500 to about 3000 rpm, or from about 1000 to about 2000 rpm. In one embodiment, the first valve opens when the device is spun at a speed of at least about 500 rpm. In alternative embodiments, the first valve 132 is opened mechanically, such as, for example, by a user. In yet another embodiment, wherein the device 100 comprises the first valve 132 and the second valve 134, both valves 132 134 open simultaneously or about simultaneously. In any embodiment, the cells 204 are separated from the suspension fluid 200 because the centripetal force forces the cells 204 from the central compartment 120 through the first valve 132 and into the intermediate compartment 124. When the suspension fluid 202 has a density equal to or lower than the density of the wash solution 206, a minimal amount of suspension fluid will pass into the intermediate compartment 124.

As the device 100 continues to rotate, the cells 204 continue to be forced through the wash solution 206 in the intermediate compartment 124, where the cells 204 become washed. Then the method includes isolating the washed cells 204 as the cells 204 pass through the aperture, opening, or second valve 134 and enter the outer compartment 126. As the cells 204 enter the outer compartment 126, the cells 204 displace the wash solution 206 that is present in the outer compartment 126 and forces the wash solution 206 through the aperture, opening, or second valve 134 in a direction opposite to that of the cells 204 and back into the intermediate compartment 124. By forcing the wash solution 206 out of the outer compartment 126, the washed cells 204 are isolated.

Figure 8:
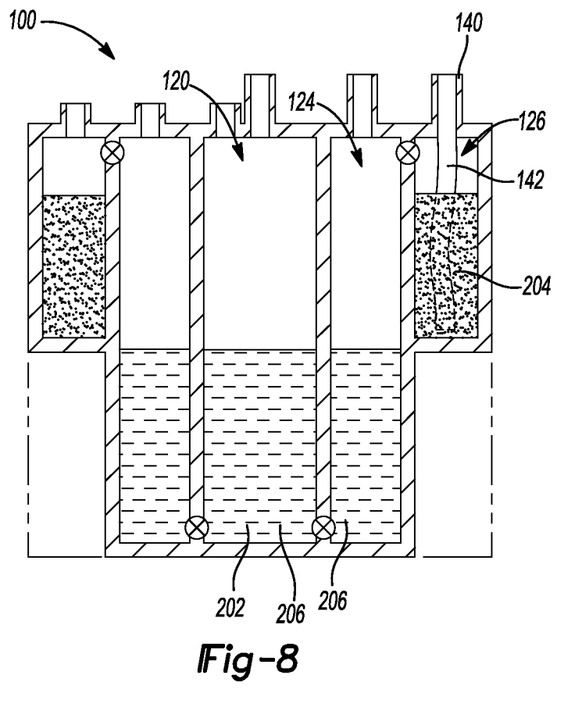

With reference to FIG. 8, rotation of the device 100 is stopped. After rotation has stopped, the device 100 contains isolated and washed cells 204 in the outer compartment 126, wash solution 206 in the intermediate compartment 124, and either suspension fluid 202 or a combination of suspension fluid 202 and wash solution 206 in the central compartment 120. The method then comprises collecting the cells 204 through the outlet 140. The conduit 142 extends into the third compartment 126 such that from about 75% to about 100% of the cells can be collected through the outlet 140. In various embodiments, at least about 90%, at least about 95%, at least about 96%, at least about 97%, at least about 98%, at least about 99%, or about 100% of the cells 204 are collected through the outlet 140. The washed cells 204 can then be administered to a subject in need thereof as they are or after being further manipulated. Alternatively, the cells can be stored as they are or further manipulated, such as with a storage solution, and stored.

Definitions

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A device for washing a suspension of cells, the device comprising:
    a cylindrical inner wall extending about and along a longitudinal axis from a first end to a second end, the inner wall defining a central compartment;
    a cylindrical intermediate wall extending about and along the longitudinal axis from the first end to the second end, the cylindrical intermediate wall defining an intermediate compartment adjacent to the central compartment;
    a cylindrical outer wall extending about and along the longitudinal axis from the first end to a third end, the cylindrical outer wall defining an outer compartment adjacent to the intermediate compartment;
    a first valve positioned through the inner wall at or near the second end such that the central compartment is in fluid communication with the intermediate compartment when the first valve is open; and
    an aperture positioned through the intermediate wall at or near the first end such that the intermediate compartment is in fluid communication with the outer compartment.

2. The device according to claim 1, further comprising a first inlet and a second inlet, the first and second inlets being positioned at the first end, wherein the first and second inlets are in fluid communication with the central and intermediate compartments, respectively.

3. The device according to claim 2, wherein the first inlet comprises a first vent and the second inlet comprises a second vent, the first and second vents configured to permit air to escape the central compartment and the intermediate compartment, respectively.

4. The device according to claim 1, further comprising an outlet positioned at the first end, wherein the outlet is in fluid communication with the outer compartment.

5. The device according to claim 4, wherein the outlet is coupled to a conduit that extends from the outlet to or near the third end.

6. The device according to claim 4, wherein the outlet comprises an third vent configured to permit air to escape the outer compartment.

7. The device according to claim 1, further comprising a first vent, a second vent, and a third vent, the vents being positioned on the first end, wherein the first, second, and third vents are in communication with the central, intermediate, and outer compartments, respectively.

8. The device according to claim 1, wherein the inner wall is sloped outwardly from the first end to the second end such that the central compartment has a diameter D1 at the first end and a diameter D2 at the second end, wherein D1 is less than D2.

9. The device according to claim 1, wherein at least a portion of the intermediate wall is slanted outwardly from or near the second end to the first end such that the outer compartment has a diameter D3 at the first end and a diameter D4 at the second end, wherein D3 is less than D4.

10. The device according to claim 1, wherein the second end and the third end are both at a distance H1 from the first end.

11. The device according to claim 1, wherein the inner and intermediate walls extend a distance H1 from the first end to the second end and the outer wall extends a distance H2 from the first end to the third end, wherein H1 is longer than H2.

12. The device according to claim 1, wherein the central, intermediate, and outer compartments are concentric.

13. The device according to claim 1, wherein the central compartment has a volume equal to or greater than a volume of the outer compartment.

14. The device according to claim 13, wherein the volume of the central compartment is greater than the volume of the outer compartment.

15. The device according to claim 1, wherein the first valve is configured to open at a predetermined centripetal force.

16. The device according to claim 1, wherein the aperture comprises a second valve, such that the intermediate compartment is only in fluid communication with the outer compartment when the second valve is open.

17. The device according to claim 1, wherein the aperture comprises a second valve configured to open at a predetermined centripetal force.

18. The device according to claim 1, wherein the first valve comprises a plurality of valves positioned though the inner wall.

19. The device according to claim 1, wherein the aperture comprises a plurality of second valves positioned through the intermediate wall.

20. The device according to claim 1, wherein the aperture comprises an annular, continuous opening.

21. The device according to claim 1, wherein the inner wall is sloped outwardly from the first surface to the second surface at an angle of from about 0.1° to about 5° with respect to the axis.

22. The device according to claim 1, wherein at least a portion of the intermediate wall is sloped outwardly from or near the second end to the first end at an angle of from about 0.1° to about 5° with respect to the axis.

23. The device according to claim 1, wherein the first valve is configured to be mechanically opened.

24. A method for washing a suspension of cells, the method comprising:
    introducing a suspension of cells into a central cylindrical compartment of a device for washing cells;
    introducing a wash solution into an annular intermediate compartment of the device, wherein the intermediate compartment is adjacent to the central compartment, and wherein the central compartment is separated from the intermediate compartment by a valve;
    rotating the device about a central longitudinal axis such that the wash solution is forced outward through an aperture and into an annular outer compartment, wherein the outer compartment is adjacent to the intermediate compartment; and
    opening the valve.

25. The method according to claim 24, wherein introducing a wash solution to the intermediate compartment comprises introducing a wash solution selected from the group consisting of water, saline, dextrose, saline with 5% dextrose, and phosphate buffered saline into the intermediate compartment.

26. The method according to claim 24, wherein introducing a suspension of cells into the central compartment comprises introducing a suspension of cells comprising an enhancement composition and a plurality of red blood cells into the central compartment.

27. The method according to claim 26, further comprising separating the red blood cells from the enhancement composition, wherein separating is accomplished when the plurality of red blood cells are caused to move through the valve and into the intermediate compartment by centripetal force and then through the aperture and into the outer compartment.

28. The method according to claim 27, further comprising isolating the red blood cells, wherein isolating the red blood cells is accomplished when the red blood cells displace any wash solution in the third compartment such that the third compartment contains only the red blood cells.

29. The method according to claim 28, further comprising collecting the red blood cells through an outlet in fluid communication with the outer compartment.

* * * * *